(12) United States Patent
Bowman

(10) Patent No.: US 9,539,022 B2
(45) Date of Patent: Jan. 10, 2017

(54) MATTER CONVEYANCE SYSTEM

(71) Applicant: MicroVention, Inc., Tustin, CA (US)

(72) Inventor: Heath Bowman, Trabuco Canyon, CA (US)

(73) Assignee: MicroVention, Inc., Tustin, CA (US)

( * ) Notice: Subject to any disclaimer, the term of this patent is extended or adjusted under 35 U.S.C. 154(b) by 216 days.

(21) Appl. No.: 14/089,521

(22) Filed: Nov. 25, 2013

(65) Prior Publication Data

US 2014/0148830 A1    May 29, 2014

Related U.S. Application Data

(60) Provisional application No. 61/730,923, filed on Nov. 28, 2012.

(51) Int. Cl.
| | |
|---|---|
| *A61B 17/22* | (2006.01) |
| *A61D 1/02* | (2006.01) |
| *A61B 17/3207* | (2006.01) |
| *A61B 17/00* | (2006.01) |

(52) U.S. Cl.
CPC .......... *A61B 17/320758* (2013.01); *A61B 17/320783* (2013.01); *A61B 2017/00685* (2013.01)

(58) Field of Classification Search
CPC .............. A61B 17/320758; A61B 17/320783; A61B 2017/00685; A61B 17/3207; A61B 2017/320775
USPC .......................................... 606/159, 170, 180
See application file for complete search history.

(56) References Cited

U.S. PATENT DOCUMENTS

| | | | |
|---|---|---|---|
| 4,857,046 A | 8/1989 | Stevens et al. | |
| 5,195,954 A * | 3/1993 | Schnepp-Pesch | A61B 17/320758 604/22 |
| 9,339,282 B2 | 5/2016 | Green et al. | |
| 2004/0219028 A1* | 11/2004 | Demarais ....... | A61B 17/320725 417/53 |
| 2009/0234378 A1* | 9/2009 | Escudero ....... | A61B 17/320758 606/180 |
| 2011/0313346 A1* | 12/2011 | Straub ............ | A61B 17/320758 604/22 |
| 2014/0194912 A1 | 7/2014 | Rice et al. | |
| 2015/0238223 A1 | 8/2015 | Zeroni et al. | |

* cited by examiner

*Primary Examiner* — Katherine M Shi
(74) *Attorney, Agent, or Firm* — Inskeep IP Group, Inc

(57) ABSTRACT

A matter conveyance system is located within a catheter and transports thrombus from a proximal portion of the catheter to a distal end of the catheter. In one example, the matter conveyance system is a screw or helix that rotates to cause movement of the thrombus.

16 Claims, 10 Drawing Sheets

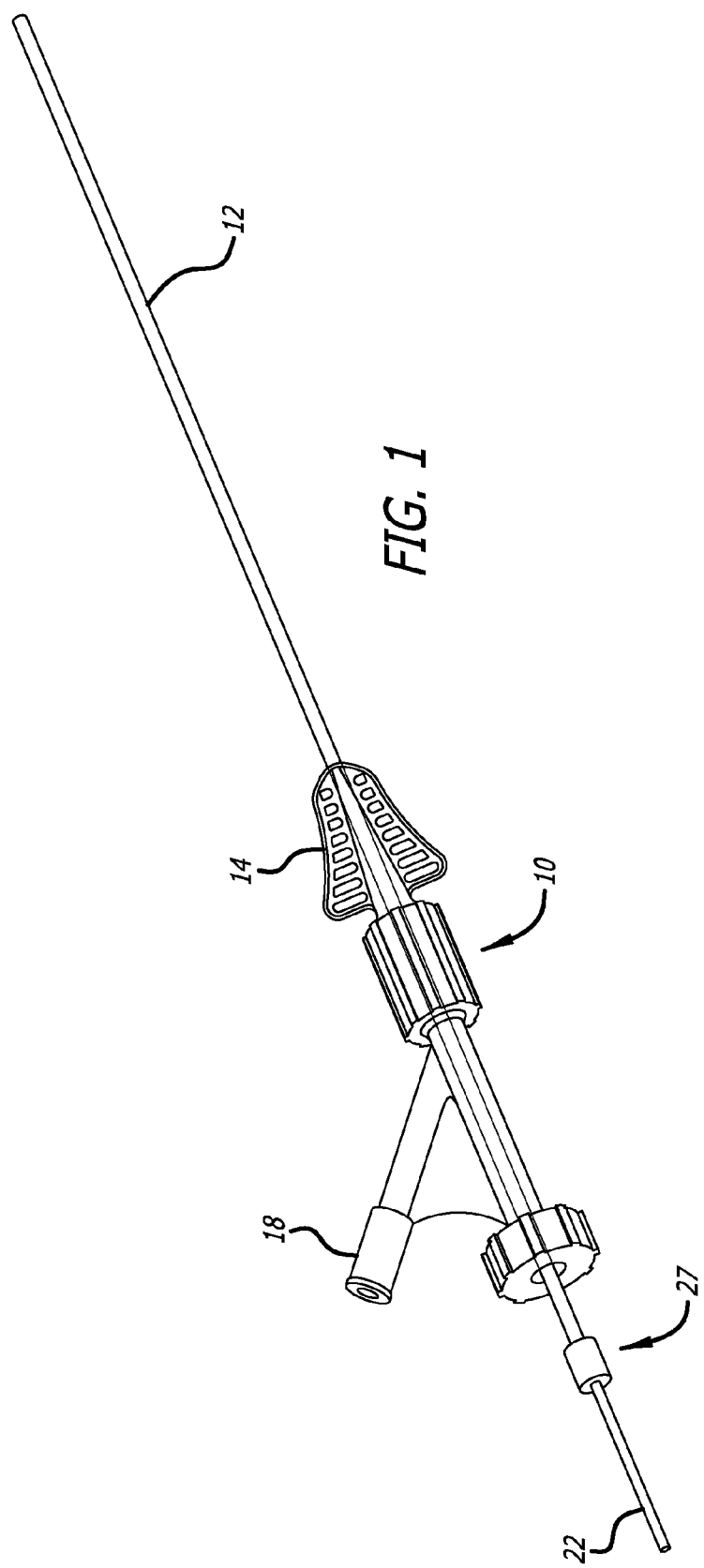

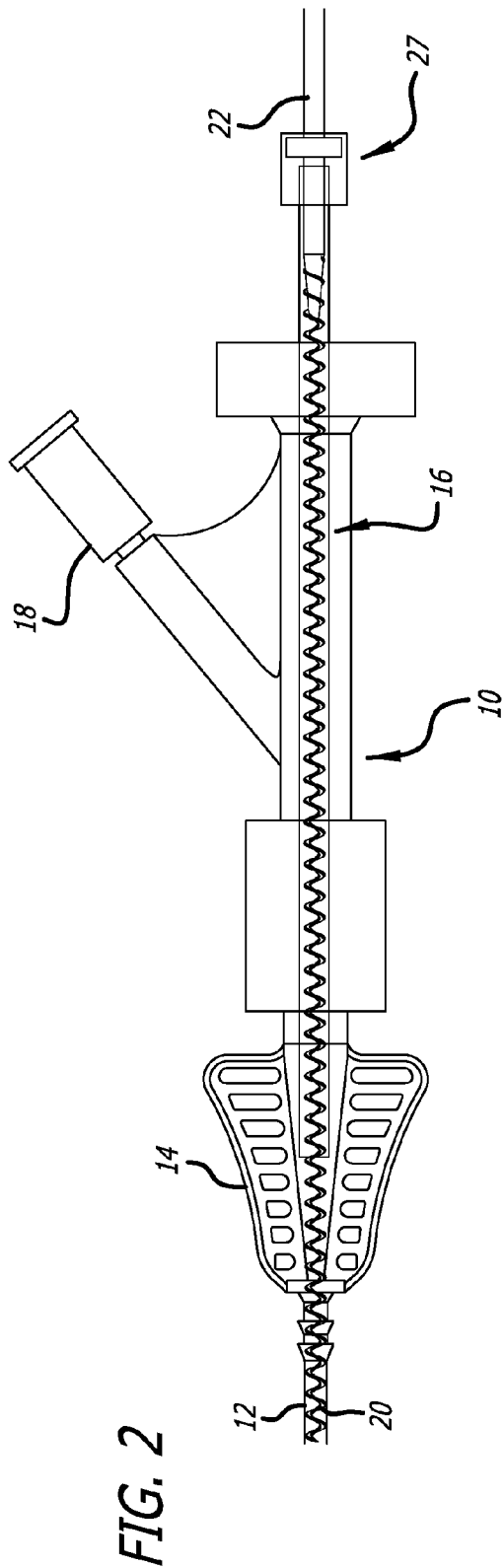

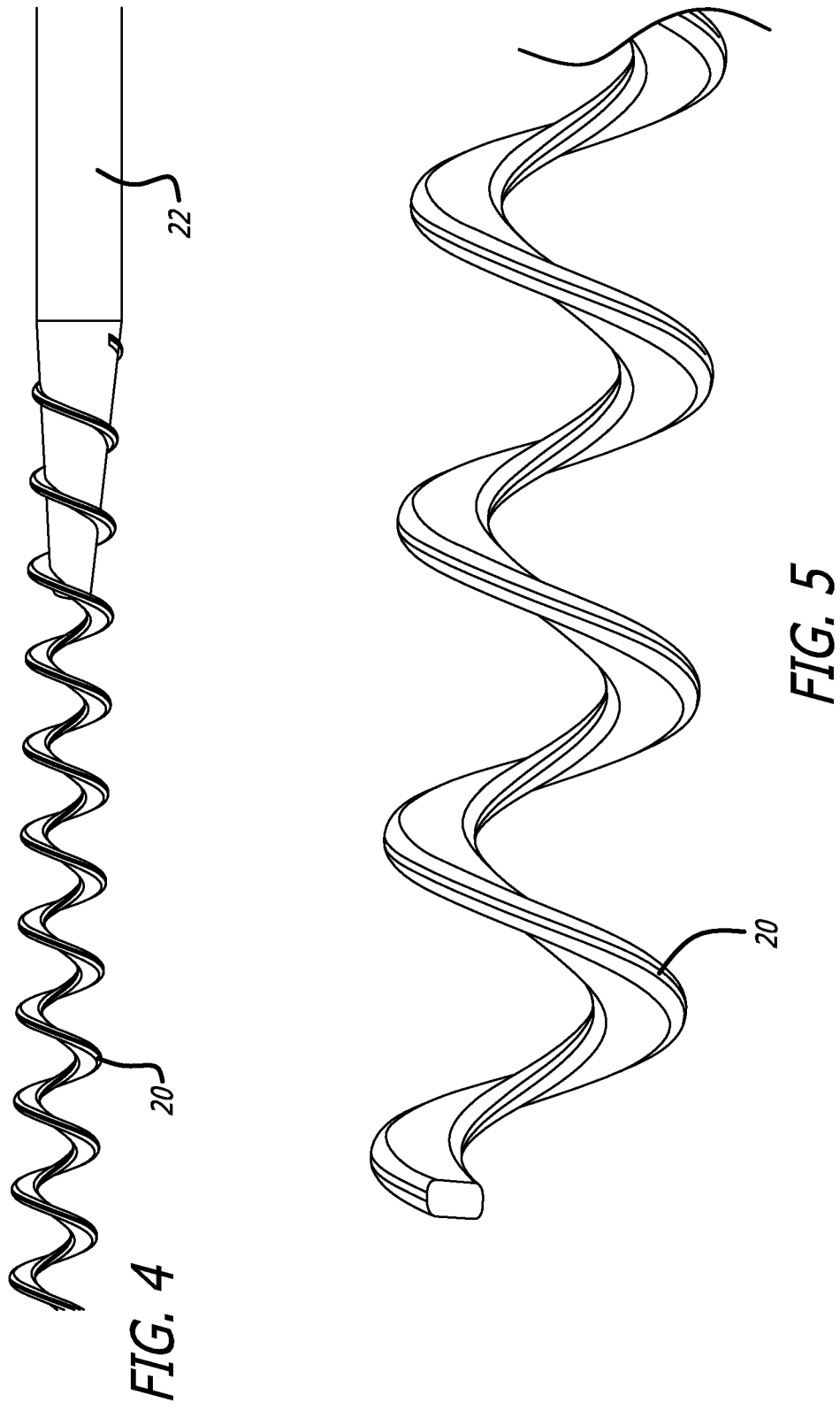

MATTER CONVEYANCE SYSTEM

RELATED APPLICATIONS

This application claims priority to U.S. Provisional Application Ser. No. 61/730,923 filed Nov. 28, 2012 entitled Matter Conveyance System, which is hereby incorporated herein by reference in its entirety.

BACKGROUND OF THE INVENTION

Buildup of thrombus in the vascular system, especially in the neurovascular system, can lead to clot formation. Clot formation can lead to disrupted blood flow, including ischemia, and may eventually lead to a stroke. Recent technologies utilize clot retrieval devices designed to grasp and remove the clot from the body. These clot retrieval devices are delivered through a delivery system, such as a catheter. Maceration or fragmentation of the clot is a significant issue during the clot retrieval and withdrawal operation. Fragmented thrombus may migrate further down the bloodstream and reform as a clot. A device which would minimize risk of maceration during clot retrieval and withdrawal operations is therefore desirable.

SUMMARY OF THE INVENTION

One embodiment of the present invention is directed to a matter conveyance system to aid in retrieval of matter and/or thrombus from the vascular system of a patient. The matter conveyance system is located within a delivery device, such as a catheter, and helps move matter through the delivery device. In one embodiment, the conveyer system includes a shaft, a screw connected to said shaft, a mechanism to rotate the shaft and screw, an introducer sleeve, and aspiration device.

The screw can be located within a substantial portion of the catheter, within only a distal portion of the catheter, beyond the distal end of the catheter tubing, or proximal to the distal end of the catheter tubing.

In another embodiment, the screw of the matter conveyance system defines a solid lumen through which other devices may be transmitted through.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which FIG. 1 illustrates a catheter utilizing a conveyer system.

FIG. 2 illustrates another view of the catheter utilizing the conveyer system of FIG. 1.

FIGS. 3-6 illustrate a screw used in a conveyer system.

DESCRIPTION OF EMBODIMENTS

Figure 6:
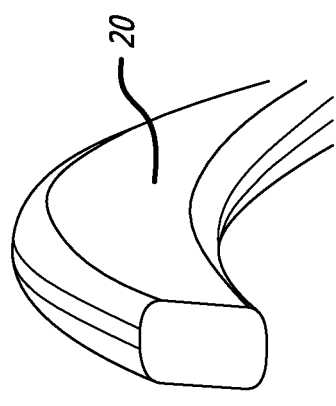

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

For purposes of terminology presented below and above, clot and thrombus can be used synonymously. Matter can refer to thrombus, clots, other obstructions, foreign body material, or other material which may be encountered within the vasculature. The terms proximal and distal as used below generally refer to areas of the catheter and/or matter conveyance system as deployed in the vasculature. Delivery device may connote catheters, sheaths, hypotubes, and the like. The term catheter can also be construed liberally as applying to sheaths, hypotube, other delivery devices, and the like.

FIGS. 1 and 2 illustrate a catheter 10 utilizing a matter conveyance system for capturing and conveying matter (e.g., a clot or other biological material within a patient's vessels) at a distal end of the catheter 10 towards its proximal end. The matter conveyance system includes a screw 20 which is located within a portion of the catheter 10 and sits within the catheter tubing 12. The screw 20 is connected to a shaft 22 that extends out a proximal end of the catheter 10, allowing for engagement with a motor for causing rotation of the screw 20. When rotated, the screw 20 functions similar to an auger or Archimedes screw, linearly moving any enclosed objects towards a proximal end of the catheter. In other words, matter pulled into the catheter tubing 12 becomes captured between the wall of the tubing 12 and the loops of the screw 20, the loops of the screw 20 to push the matter in a proximal direction as the screw rotates.

In one example, aspiration (i.e. suction) can be used to pull the matter within the distal end of the catheter's tubing 12 and further assist the rotation of the screw 20 to displace the matter proximally through the catheter. In one example, the aspiration can be applied by advancing a smaller diameter tube into port 18 and through the catheter 10 to a point just external of the catheter's distal end, thereby allowing the suction to engage the matter. In this regard, the tube can subsequently be retracted (or simply left in place and deactivated) and the rotation of the screw used to displace the clot or matter proximally through the catheter 10. Alternatively, the aspiration tube can be applied near a proximal end of the catheter tube 12 (e.g., directly to port 18), thereby assisting the screw 20 in displacing the matter through the rest of the catheter 10.

In one example, the shaft 22 and screw 20 are separate components which are mated together by a process such as welding, or other adhesive or bonding techniques. In another example a tube can be processed to create an integral shaft and screw component, such as via laser-cutting, etching or similar techniques.

The screw 20 may take on a variety of shapes and/or angles in its profile, including a helix, and/or the traditional spiral shape common to augers/Archimedes screws. Preferably, the screw 20 is shaped such that it forms an internal passage, lumen, or throughway 21 along its length, as seen in FIGS. 3-6 and particularly in FIG. 13. This lumen 21 allows devices, such as a guidewire or an aspiration tube to pass through both the screw 20 and the catheter 10 during various portions of a procedure.

In the embodiment of FIGS. 3-6 and 13, the lumen 21 is formed entirely from the loops of the screw. However, a closed lumen configuration is also possible, in which a cylindrically (or other) shaped lumen surrounds the external screw diameter. In other words, the threads of the screw 20 could be fixed against an outer tube that rotates with the screw threads. Such an outer tube may extend along the entire length of the screw threads or a fractional length.

For example, the lumen could extend from the distal end of the shaft 22 to the distal end of the screw 20. Alternately, it could extend from the distal end of the shaft 22 to a point before the distal end of the screw 20. Alternately, it could extend from any point proximal from the distal end of the screw 20 to the distal end of the screw 20. Alternately still, the outer lumen could be segmented along the length of the screw 20. The closed lumen screw configuration could be formed by placing a hollow tube external to the screw and mating the pieces together by welding or other techniques. Alternately, the screw configuration could be cut from the tube, leaving a closed lumen with a screw pattern formed therein via laser cutting or similar techniques. In another example, the shaft 22 also has a lumen to accommodate various devices (e.g. a guidewire), such that a device can pass through the shaft 22 and into the lumen of the screw 20.

The screw 20, outer tube, and shaft 22 can be made from a variety of materials including but not limited to tempered spring steel, stainless steel, similar metals, or a variety of polymers including polyethylene, UHMWPE, PVC, ABS, etc.

Returning to FIGS. 1-2, the catheter tubing 12 includes a luer adapter 14 connected to hemostasis or hemostatic valve 16. The hemostatic valve 16 contains a port 18 that can be used with an air source for aspiration (as previously discussed) or to inject contrast to aid in visualization. Hemostatic valve 16 and luer adapter 14 both have a lumen running through them to accommodate the matter conveyance system.

Screw 20 can be located along the entire length of the catheter or any fractional portion thereof. For example, the distal end of the screw 20 may be located at or near the distal end of the catheter tubing 12, while the proximal end of the screw 20 may be located at or near the proximal end of the hemostatic valve 16.

Figure 14:
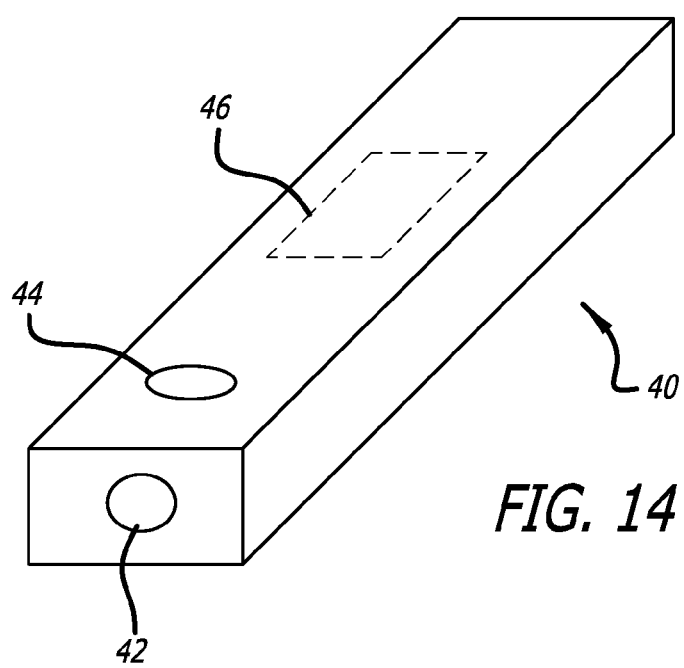
FIG. 14 illustrates a motorized device for rotating a conveyer system.

The proximal end of the screw 20 preferably connects to shaft 22 (seen best in FIGS. 1-4) at a proximal portion of the catheter 10 such that the shaft 22 extends out of the catheter's proximal end. In one embodiment, the shaft 22 is connected to a handheld device 40, shown in FIG. 14 for the purposes of rotating shaft 22 and screw 20. Preferably, the device 40 includes a motor 46 that is engaged with the shaft 22, and a button 44 for starting and stopping rotation. Optionally, the device 40 may also include a button or switch for changing a direction of rotation of the screw 20. In one embodiment, the shaft 22 can be inserted into and removed from an aperture 42 on the device 40. In another embodiment, the shaft 22 is permanently fixed to the device 40 and cannot be removed by the user.

In another embodiment, the handheld device 40 further comprises a non-electrical, manual, mechanical rotation mechanism, such as a hand-crank, dial, or outer rotating tube. The handheld device 40 may include this mechanical rotation mechanism on its own or as a secondary mechanism in addition to the previously described motor 46.

Figure 7:
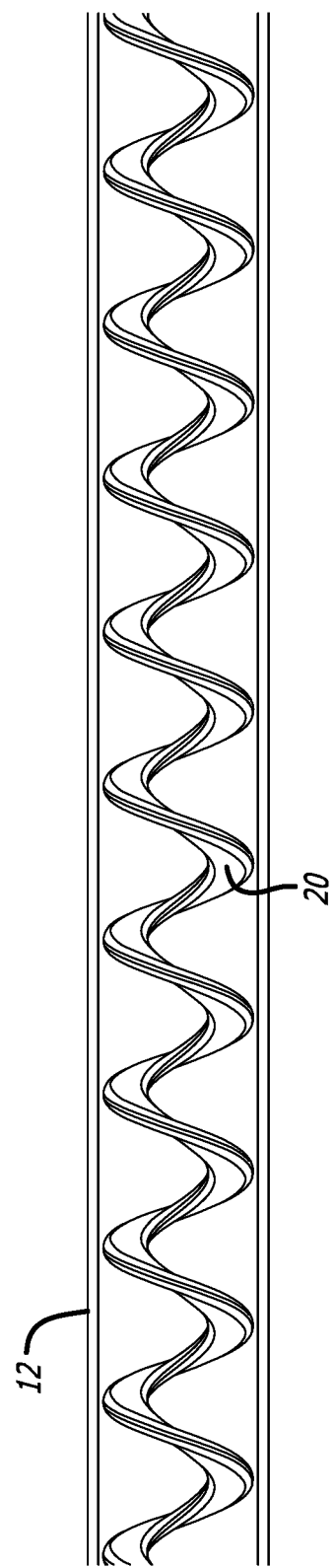
FIG. 7-11 illustrate various sections of the catheter utilizing the conveyer system of FIG. 2.

Turning to FIG. 7, the distal end of the catheter 10 includes catheter tubing 12 which has an internal passage with a larger diameter than the outer diameter of the screw 20, thereby allowing the screw 20 to rotate. The screw 20 extends through the length of the tubing 12, through the hemostatic valve 16, and merges into the shaft 22 shortly before a flared end 30. However, the length of the screw section and shaft section can be customized.

Figure 8:
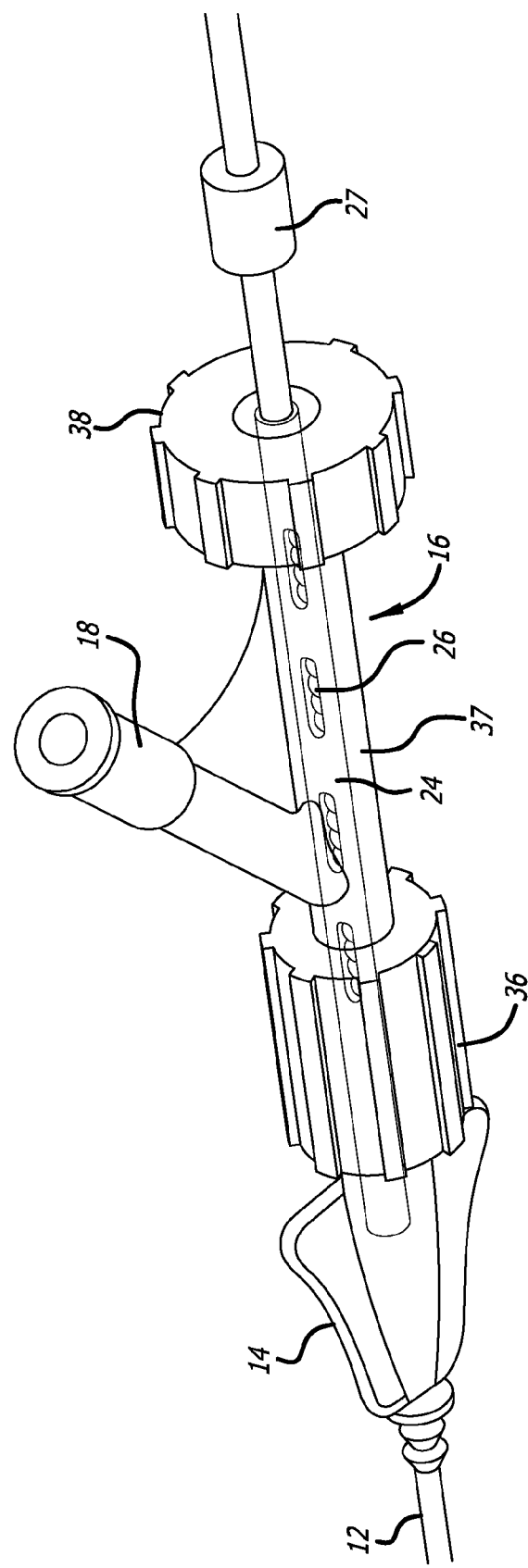

As best seen in FIGS. 1, 2, and 8, the luer adapter 14 connects the catheter tubing 12 with the hemostatic valve 16. Specifically, the distal end of the luer adapter 14 is connected to the proximal end of the catheter tubing 12 while the proximal end of the luer adapter 14 is connected to the hemostatic valve 16.

As best seen in FIG. 8, the hemostatic valve 16 allows various devices, such as a guidewire, the screw 20, and the introducer sleeve 24 to enter the catheter tubing 12 without substantial proximal blood leakage. While a wide variety of different hemostatic valves can be used according to the present invention, the present embodiment of the hemostatic valve 16 is generally known as a Y-adapter valve since it includes a main body portion 37 and a secondary port 18. The valve 16 further includes a luer lock portion 36 at the distal end of the body portion 37 that engages the luer adapter 14 and further contains a seal. An adjustable valve 38 is located at the proximal end of the body portion 37, allowing the end of the body portion 37 to be sealed off completely when not in use or to seal around an inserted device.

The main body portion 37 of the hemostatic valve 16 contains a channel sized to accommodate an introducer sleeve 24 (best shown in FIGS. 8-12) that is inserted into the channel to provide a guide path and to allow rotation of screw 20. The slots 26 of the introducer sleeve 24 allow for aspiration via port 18 to aid in pulling the matter through the catheter 10 while also providing visibility within the sleeve 24 to determine whether or not the matter has been pulled into the hemostatic valve 16. In one embodiment, the introducer sleeve 24 is a hypotube with a number of slots 26 located along the length of the sleeve 24 in one or more rows (e.g., 2 or 4 rows on opposite sides of the sleeve 24). The introducer sleeve 24 may be made out of various materials such as stainless steel or a rigid polymer.

The conveyance system further includes a seal assembly 27 (seen best in FIGS. 10 and 11), which ensures that contrast or other lytic agents can be injected through the catheter 10 (via port 18) without the need to remove the matter conveyance system. Seal assembly 27 also ensures that any aspiration (via port 18) used to help pull the matter through the system will be effective at creating suction. The seal assembly 27 creates a pressure buildup at the proximal-most end of the system, therefore allowing any lytic agents to naturally flow distally—or away from—seal assembly 27 and towards catheter tubing 12. Similarly, any aspiration or negative air pressure source used to aid in retrieval operations will pull in a direction from the catheter tubing 12 towards the seal assembly 27, in a distal to proximal direction.

In the present embodiment, the seal assembly 27 includes a cylindrical housing 28 having a circular slot 28A sized for a seal member 30. The seal member 30 is positioned such that it engages and seals against the shaft 22, thereby preventing any fluid from moving out of the end of the sleeve 24. In one embodiment, the seal assembly 27 could be connected to or integrated with the handheld device 40.

Figure 11:
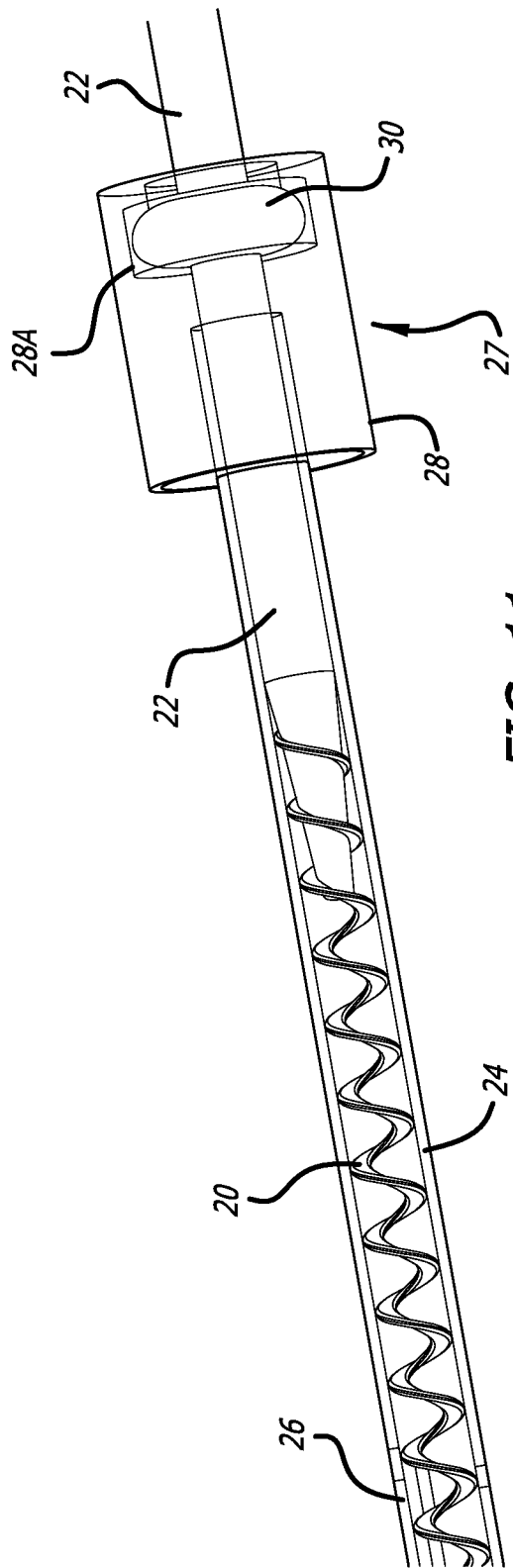
Figure 12:
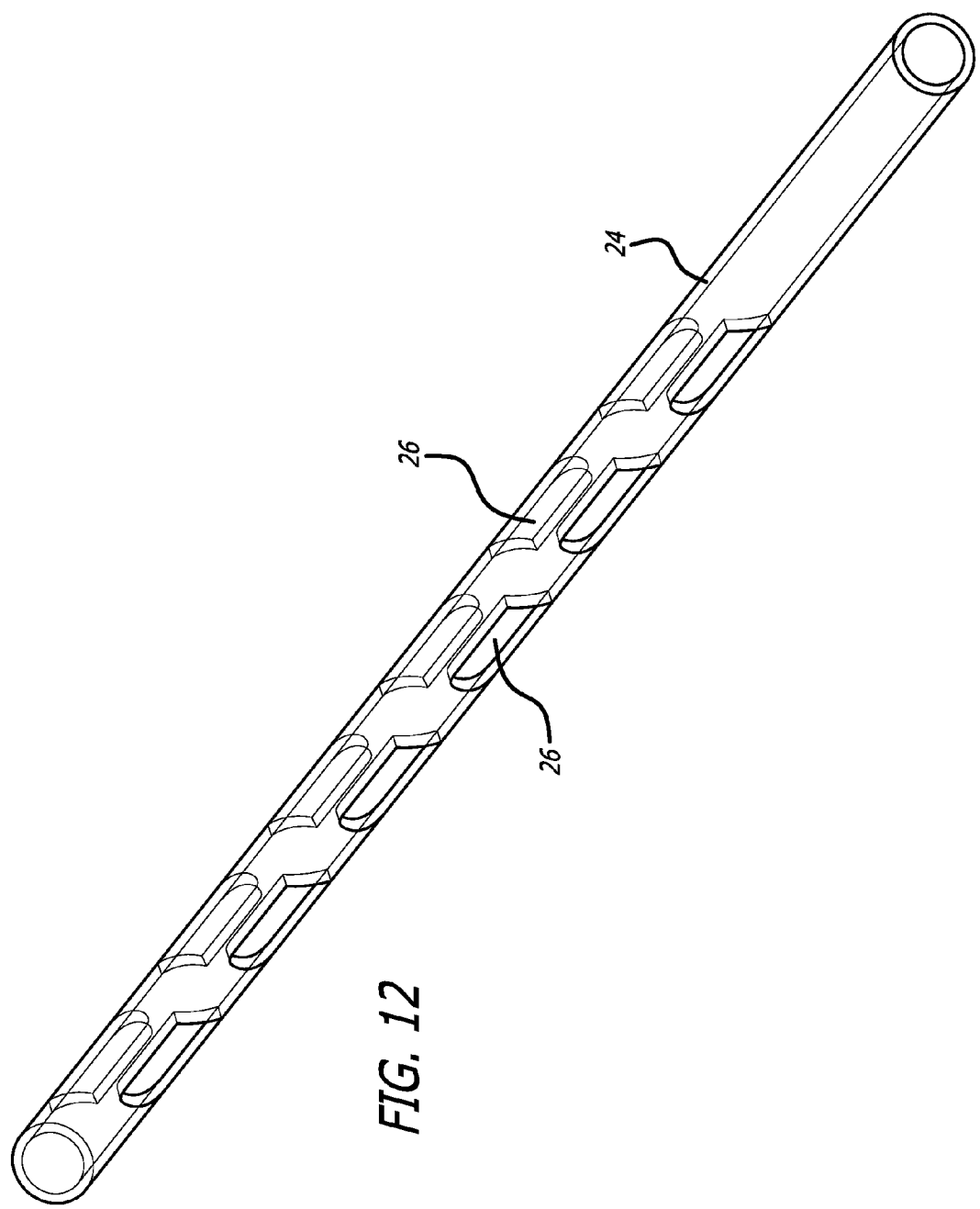
FIG. 12 illustrates an introducer sleeve used in a conveyer system.
Figure 13:
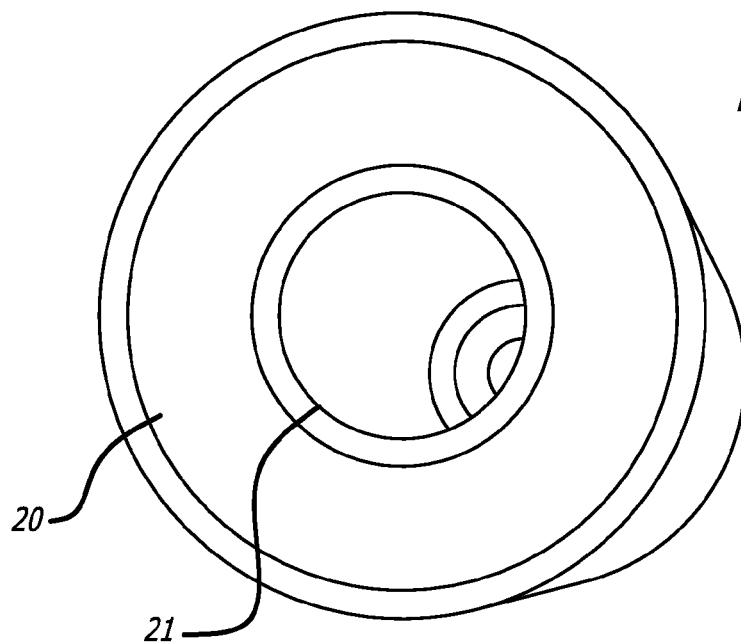
FIG. 13 illustrates an end view of the screw shown in FIGS. 3-6.

In one embodiment, the matter conveyance system sits within a guide catheter and thus avoids the need of a microcatheter to deliver and retrieve a clot retrieval device. A guidewire can also be used with the system as follows. Due to the shape of the screw 20 (as shown in FIGS. 11 and 13) which leaves a large center region open 21, the guidewire can pass through the screw 20.

Figure 9:
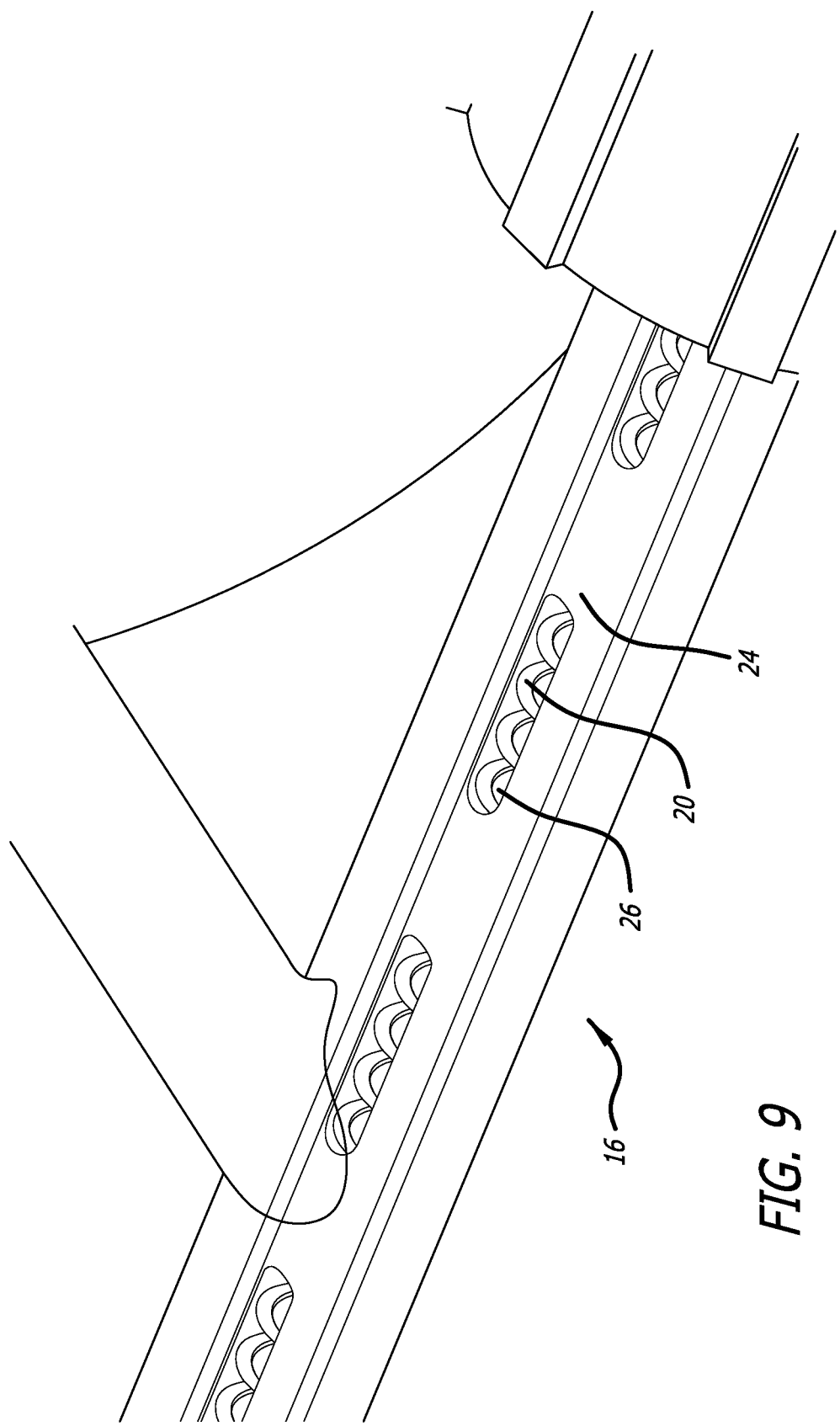
Figure 10:
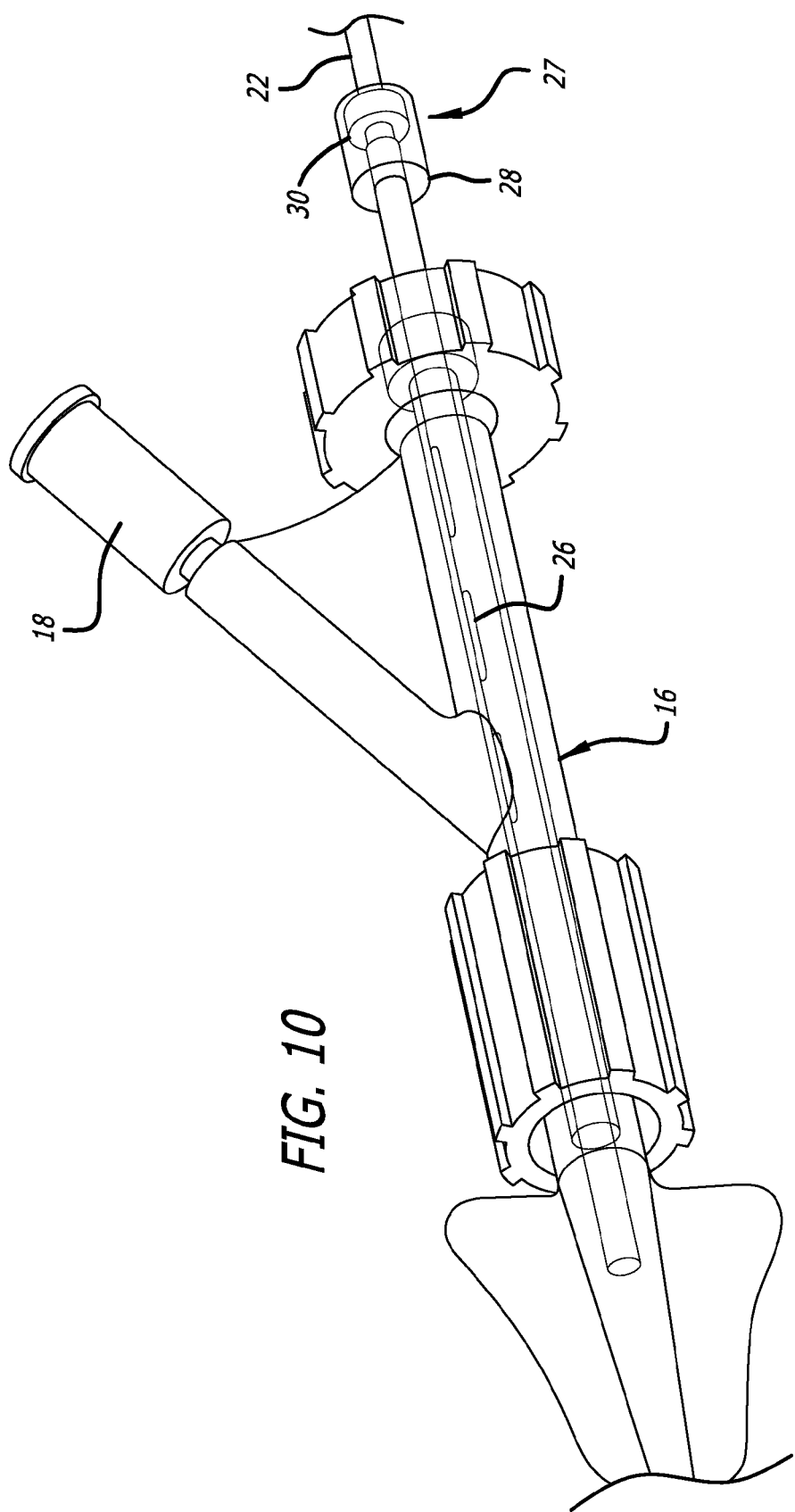

Referring to FIGS. 8-9, a guidewire can be advanced through port 18 and into the introducer sleeve can be rotated/manipulated such that slot 26 of introducer sleeve 24 corresponds with the through-hole of port 18 so that an inserted guidewire will pass through slot 26. The guidewire can then be pushed through the guide catheter 10 and will pass through the open center region of the screw all the way past the distal end of the microcatheter 10. When the aspiration means are used to provide suction to engage the thrombus, and the thrombus is engaged and brought back to the distal end of the guide catheter, the conveyance system can be activated to pull the thrombus all the way back through the catheter 10.

Alternatively, another RHV (rotating hemostatic valve) can be placed distal to the motor, and the guidewire can be placed through a port on this more distal RHV. In this configuration a lumen will run through the complete length of the system so that the guidewire can pass through the length of the screw 20 (i.e. the open-channel screw would run all the way from the proximal end to the distal end of the matter conveyance system).

In another embodiment, the matter conveyance system can be used in a smaller sheath that is delivered through a guide catheter. A sheath, hypotube, smaller catheter, or microcatheter can be placed through the guide catheter. Such a configuration might be useful for engaging smaller regions of matter or thrombus buildup. Aspiration means may be delivered through the microcatheter to engage the matter or thrombus, and the screw may be used to move the matter or thrombus through the microcatheter.

In another embodiment, a portion of the screw in the matter conveyance system can utilize a solid, hypotube profile while still retaining the inner open lumen to preserve accessibility of the guidewire through its center passage. The hypotube section will provide some increased structural strength to the entire screw due to the more rigid profile shape. In one example, the entire screw is laser-cut and the hypotube section is laser-cut to a lesser extent, leaving a solid-channel hypotube section and an open-channel screw section.

Another embodiment involves only a distal portion of screw 20 functioning to convey matter. In this embodiment, shaft 22 could be extended such that screw 20 runs through only a distal portion of the device (i.e. only through a portion of the tubing 12). Alternatively, a hypotube could be placed over the proximal portion of screw 20 leaving only the distal portion of the screw 20 with the configuration which will allow conveyance. In this embodiment, the screw is used to convey the matter from only a distal portion to more proximal portion of the catheter (instead of all the way through the catheter). The catheter could be removed entirely from the vasculature to remove the matter once the matter reaches a proximal portion of the catheter.

In another embodiment, screw 20 may extend past the distal end of catheter tubing 12. This configuration would enable the screw 20 to grasp matter within the matter conveyance system before said objects enter the catheter, then help move said objects through the catheter. This configuration could also be useful for using screw 20 as a clot disruptor. Since screw 20 extends past distal end of catheter tubing 12, it would be positioned in the vasculature. Thus it could engage with a clot or matter, allowing rotation of the screw to extract a portion of the clot as well as convey the engaged clot to a proximal position within the catheter via the matter conveyance system.

In another embodiment screw 20 may not run all the way through the distal end of catheter tubing 12. In this configuration, matter would be pulled through a portion of the catheter, until engaged with screw 20, and then is conveyed through the catheter via the matter conveyance system.

In another embodiment, the inner diameter or passage 21 of screw 20 may define another interior lumen used to deliver other devices. In one example, the inner lumen 21 is machined when creating the screw to introduce an inner lumen 21 consistent with the material used to make the screw.

In another example, the screw has a permanent polymer or metallic lumen affixed within the inner diameter/passage 21 of the screw which functions similar to a microcatheter positioned within the guide catheter. This lumen could extend throughout the entire length of the screw, or just along a more proximal portion of the screw. In another example, the inner screw diameter 21 accommodates a removable microcatheter which can be pushed through and pulled out of the interior of the screw. This lumen may be used to deliver the guidewire and may also be used to deliver a clot retrieval device. Such clot retrieval devices may be mechanical systems used to physically grasp the clot and are typically delivered through a microcatheter. With this embodiment the inner lumen of the screw would act like a microcatheter and could be used to deliver a clot retrieval device to a particular site within the vasculature. The aspiration means could also be delivered through this closed lumen.

In one example, the outer screw diameter is between about 0.017" to 0.068". Since the screw fits within the catheter 10, the catheter inner and outer diameter will be larger than the screw diameter. Thus, in one example, the screw 20 fits in a catheter 10 sized anywhere from about 0.021" for the outer diameter to about 0.09" for the outer diameter. The pitch of the screw 20 can be as low as almost zero (closed pitch) to about 0.2". The screw thickness can be about 0.005" to 0.5". In one example the screw pitch is about 0.07", thickness is about 0.02", the outer diameter is about 0.068" and inner diameter (found by subtracting the overall screw lumen thickness from the outer diameter) is about 0.028". These values are offered up as illustrative examples and are not meant to define or limit the matter conveyance system in any way.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A biological conveyance system, comprising:
an elongated screw having a proximal end and a distal end; said elongated screw locatable within a catheter;

a rotation mechanism coupled to said proximal end of said elongated screw and configured to rotate said elongated screw so as to retract biological material located within a patient;

a catheter sleeve in which said elongated screw is located;

a hemostasis valve coupled to a proximal end of said catheter sleeve; and, an introducer sleeve in which said elongated screw is located, said introducer sleeve being located within said hemostasis valve and having a plurality of slots exposing an interior of said introducer sleeve with an exterior of said introducer sleeve, wherein said plurality of slots are located adjacent to an aspiration port such that said aspiration port is in communication with said interior of said introducer sleeve and thereby aspirate said biological material from said interior of said introducer sleeve.

2. The biological conveyance system of claim 1, wherein said elongated screw has a helix shape that forms an internal passage along a length of said elongated screw.

3. The biological conveyance system of claim 1, wherein said distal end of said elongated screw is positioned within and proximate to a distal end of said catheter sleeve.

4. The biological conveyance system of claim 1, wherein said elongated screw further comprises a shaft fixed to said proximal end of said elongated screw and to said rotation mechanism.

5. The biological conveyance system of claim 1, wherein said catheter sleeve connects to said hemostasis valve via a luer.

6. The biological conveyance system of claim 1, wherein said hemostasis valve is Y-adapter valve.

7. The biological conveyance system of claim 6, further comprising a seal adapter located on said proximal end of said screw and a proximal end of said slotted sleeve.

8. The biological conveyance system of claim 7, wherein said aspiration device is connected to a secondary port on said hemostasis valve.

9. The biological conveyance system of claim 1, wherein said rotation mechanism comprises a motorized rotation mechanism, a non-motorized rotation mechanism, or both.

10. A thrombus transport system, comprising:
a catheter;
an elongated helical member rotatably-positioned within said catheter;
a hemostasis valve coupled to a proximal end of said catheter;
an introducer sleeve in which said elongated helical member is located, said introducer sleeve being located within said hemostasis valve and having a plurality of slots exposing an interior of said introducer sleeve with an exterior of said introducer sleeve, wherein said plurality of slots are located adjacent to an aspiration port such that said aspiration port is in communication with said interior of said introducer sleeve and thereby aspirate biological material from said interior of said introducer sleeve;
wherein a distal end of said elongated helical member is located near a distal end of said catheter.

11. The thrombus transport system of claim 10, wherein said elongated helical member has a proximal end located near a proximal end of said catheter.

12. The thrombus transport system of claim 10, further comprising a handheld rotation device coupled to a proximal end of said elongated helical member so as to cause rotation of said elongated helical member.

13. The thrombus transport system of claim 12, further comprising an aspiration device connected to said aspiration port.

14. The thrombus transport system of claim 10, wherein said elongated helical member further comprises a passage along a length of said elongated helical member that is sized to allow passage of a guidewire.

15. The thrombus transport system of claim 10, further comprising an outer tube fixed over an outer surface of said elongated helical member.

16. A method of transporting biological material from a patient, comprising:
advancing a distal end of a catheter to a target location;
engaging biological material with a screw member located within said catheter;
rotating said screw member such that said biological material moves from said distal end of said catheter to a hemostatic valve near a proximal end of said catheter;
applying suction through said hemostatic valve and removing said biological material through a plurality of apertures in an introducer sleeve that is positioned over a portion of said screw member, wherein said introducer sleeve is located within said hemostatic valve.

* * * * *